United States Patent [19]
Akima et al.

[11] Patent Number: 5,981,509
[45] Date of Patent: Nov. 9, 1999

[54] PREPARATION FOR PROPHYLAXIS OR TREATMENT OF RENAL DISEASES CONTAINING SULFATED POLYSACCHARIDE

[75] Inventors: Kazuo Akima, Yokohama; Kenichi Shikata, Okayama; Hirofumi Makino, Okayama; Zensuke Ota, Okayama; Kyoji Hirata, Okayama; Masayuki Miyasaka, Suita; Yasuo Suzuki, Shizuoka, all of Japan

[73] Assignee: Shiseido Company, Ltd., Japan

[21] Appl. No.: 08/859,293

[22] Filed: May 20, 1997

[51] Int. Cl.[6] ....................... A61K 31/715; A61K 31/725
[52] U.S. Cl. ................................ 514/54; 514/56; 514/59; 514/53
[58] Field of Search ................................ 514/54, 56, 59, 514/53

[56] References Cited

U.S. PATENT DOCUMENTS 4,840,941  6/1989  Ueno et al. ................................ 514/59

FOREIGN PATENT DOCUMENTS 58-56692  4/1983  Japan.
2-7577   2/1990  Japan.

OTHER PUBLICATIONS

K. Kawasaki et al., *J. Immunol.*, 150(3), 1074–1083 (1993).
U. von Andrian et al., *Proc. Natl. Acad. Sci. USA*, 88, 7538–7542 (1991).
G. Schreiner et al., *Kidney International*, 34, 487–493 (1988).
R.H. Heptinstall, *Pathology of the Kidney*, R.H. Heptinstall, ed., 3, 1489–1562 (1991).

*Primary Examiner*—Gary L. Kunz
*Assistant Examiner*—Everett White
*Attorney, Agent, or Firm*—Wenderoth, Lind & Ponack, L.L.P.

[57] ABSTRACT

The specification relates to a preparation for the prophylaxis or treatment of renal diseases, and a method for the prophylaxis or treatment of renal diseases, and specifically, it relates to the above preparation and method using a sulfated polysaccharide as an active ingredient.

8 Claims, No Drawings

PREPARATION FOR PROPHYLAXIS OR TREATMENT OF RENAL DISEASES CONTAINING SULFATED POLYSACCHARIDE

BACKGROUND OF THE INVENTION

This invention relates to a pharmaceutical preparation for renal diseases, and more specifically, relates to a pharmaceutical preparation containing a sulfated polysaccharide. Further, the invention relates to a method for the prophylaxis or treatment of a renal disease which comprises administering a sulfated polysaccharide to a patient suffering from the renal disease.

Renal diseases are, usually, such diseases that renal functions are lowered progressively, resulting in renal failure. A certain extent of therapeutic efficacy by the use of a steroid agent or an immunosuppressant is recognized on renal diseases based on certain causes, but renal diseases not fit for treatment by steroid agents are hard to cure and it is said that such renal diseases develop to renal failure in the course of time. In this connection, it is the present state of things that even when a renal disease is fit for treatment by a steroid agent, its use is restricted because it causes side effects in a high frequency, and thus it is mainly treated by dietetics.

Further, there is a report wherein a certain renal disease, for example an autoimmune renal disease is grasped from the viewpoint of inflammation, attention is payed to the action of an adhesive molecule, and it is attempted to suppress the inflammation by an antibody against ICAM-1 (J. Immunol. 150, 1074–1083, 1993).

On the other hand, as publications wherein the application of sulfated polysaccharides used in the invention to pharmaceuticals is described, there is Japanese Patent Publication No. 7577/1990. It is disclosed in this official gazette that sulfates of various saccharides including salfated hyaluronic acid can be used for the treatment of human immunodeficiency viral diseases. However, the official gazette does not describe nor suggest that not only these polysaccharides can be used as anti-inflammatory agents, but they can be used as agents for the treatment of renal diseases.

As is seen from the foregoing, it is the present state of things that it can be said that pharmaceuticals which can be used safely for the prophylaxis or treatment of renal diseases have not yet been provided. Thus, the object of the invention lies in providing a pharmaceutical preparation which can be used more safely for the prophylaxis or treatment of renal diseases, and moreover has significantly excellent efficacy.

In recent years, the importance of the adhesive molecule in inflammatory reactions has gradually understood due to the rapid progress of researches into adhesive molecules. In view of the roles of adhesive molecules, for example, L-selectin molecules in inflammation, it is known that L-selectin is expressed in various leukocytes including neutrophiles, T and B lymphocytes and monocytes, and plays a role to make those mononuclear cells flowing with rapid force in the blood gently roll on the hemal endothelial cells (von Andrian et al., Proc. Natl. Acd. Sci. U.S.A. 88, 7538–7542, 1991). It is said that then, the mononuclear cells bind tight to the endothelial cells, and infiltrate into tissues through the endothelial interstitium.

As to the renal tissue, it is reported that the ureteral obstruction of a laboratory model rat can be an initial model for the analysis of the mechanism of tissue infiltration by mononuclear cells and for some renal diseases (for example, Schreiner, G. F. et al., Kidney Int. 34, 487–493, 1988, and Heptinstall R. H. in Pathology of the Kidney (edited by Heptinstall), 1489–1562, 1991).

SUMMARY OF THE INVENTION

When it is taken into account that the tissue infiltration of mononuclear cells plays an important role even on the exacerbation of renal diseases, a possibility is extremely high that a substance capable of reducing the tissue infiltration of mononuclear cells in the above laboratory animal model is a promising pharmaceutical for the treatment of renal diseases. Thus, the present inventors carried out a screening for effective substances in the above experimental model system, and found that sulfated polysaccharides significantly reduce the tissue infiltration of mononuclear cells.

Thus, the above object can be attained by a preparation for the prophylaxis or treatment of a renal disease which comprises a sulfated polysaccharide in an amount effective for the prophylaxis or treatment of the renal disease, and pharmaceutically acceptable diluent(s) or carrier(s), and a method for the prophylaxis or treatment of a renal disease which comprises administering an effective amount of a sulfated polysaccharide to a mammal.

DESCRIPTION OF THE PREFERRED EMBODIMENT

The sulfated polysaccharide usable in the invention includes both of natural ones and semisynthetic or synthetic ones so long as they are fit for the object of the invention. Although not limited thereto, as specific ones of these polysaccharides, there can be mentioned sulfated acid mucopolysaccharides and sulfated dextran.

The sulfated acid mucopolysaccharide means a long-chain polysaccharide having a repeating unit of a disaccharide composed by a hexosamine (in many cases, N-acetylated glucosamine or N-acetylated galactosamine) and an uronic acid (D-glucuronic acid or L-iduronic acid) and having sulfate radicals. Since some natural acid mucopolys;accharides have sulfate radicals, they themselves, and those obtained, if desired, by further chemically sulfating these natural ones are included in the sulfated acid mucopolysaccharide of the invention. Further, acid mucopolysaccharide having no sulfate radical come to be usable in the invention by chemically introducing sulfate radicals.

Specific examples of these acid mucopolysaccharides are chondroitin 4-sulfate and 6-sulfate, dermatan sulfate, heparan sulfate, heparin sulfate and keratan sulfate as those having sulfate radicals, and hyaluronic acid and chondroitin as those having no sulfate radicals.

As specific examples of the sulfated dextran, there are also included partial sulfate esters which are known to have a heparin-like anticoagulant action and are used clinically.

Among the above various sulfated saccharides, sulfated hyaluronic acid is particularly preferable from the viewpoint of availability of its starting material and efficacy. Sulfated hyaluronic acid is a compound obtained by sulfating hyaluronic acid (a straight-chain high molecular polysaccharide formed by alternate bond of β-D-N-acetyglucosamine and β-D-glucuronic acid) derived from comprehensive natural sources, for example connective tissues of mammals, cockscombs of chickens, gastroantral membranes of silkworms, capsules of streptococci, etc. Since although as to hyaluronic acid varience of molecular weight generally exists depending on the kind of sources, ununiformity on structure is not known, hyaluronic acid of any source can be used. However, in view of availability, hyaluronic acid derived from streptococci, although not limited thereto, can conveniently be used. A specific example thereof is hyaluronic acid prepared according to a process as described in Japanese Laid-Open Patent Publication No. 56692/1983. This has, in general, a molecular weight of about 2,000 kDa. Hyaluronic acid can, if desired, be adjusted for molecular weight by partial hydrolysis or the like known per se. when the rapid action of the final product is expected, one having a low molecular weight (hereafter abbreviated as LMWHA) is used for the succeeding sulfation treatment, and when the prolonged action thereof is expected, one having a high molecular weight (hereafter abbreviated as HMWHA) is used therefor.

Although hyaluronic acid can be sulfated according to a process known per se, a process comprising using a sulfuric acid-trimethylamine complex as a sulfating agent is preferable. The use ratio between hyaluronic acid and a sulfating agent can freely be chosen in accordance with the sulfation rate (or sulfur content) of the desired sulfated hyaluronic acid and the reaction conditions. In general, when the reaction is carried out at a temperature of 50 to 60° C. over a period from scores of hours to several days, the amount of the sulfating agent is chosen so as to be about two times by weight that of hyaluronic acid. The thus attained sulfation rate is generally about 50 to 60% of the total hydroxyl groups of hyaluronic acid.

The resultant sulfated hyaluronic acid can be purified according to purification operations conventionally used for various modified polysaccharides. Specific purification operations include steps of concentrating the reaction mixture under reduced pressure, dialyzing the concentrate against water to desalt it, removing triinethylamine by trifluoroacetic acid treatment and freeze-drying the residue. Other acid mucopolysaccharides can also be converted to the corresponding sulfated acid mucopolysaccharides in the same manner as in the above sulfation treatment of hyaluronic acid. Although the optimal values of their molecular weight and sulfation rate vary depending on the kind of the saccharides, a person skilled in the art can readily choose these optimal values through the later-described efficacy test, etc.

The sulfated acid mucopolysaccharide or sulfated dextran can, if desired, be used in the form of a physiologically acceptable salt obtained by reaction with a hydroxide or carbonate of an alkali metal, or an amine or the like.

The above sulfated acid mucopolysaccharide or sulfated dextiran or a physiologically acceptable salt thereof can be mixed with diluent(s) or excipient(s) used for preparation of usual pharmaceutical preparations to give liquids or suspensions which can then be administered arenterally, e.g. intravenously, intraarterially or intraperitoneally. Diluent(s) or excipient(s) usually used in the liquids include, for example, water, ethyl alcohol, propylene glycol, etc., and those in the suspensions include polyoxyethylenesorbitol and sorbitan esters.

The optimal mixing ratio between the diluent(s) or excipient(s) and the sulfated acid mucopolysaccharide or sulfated dextran is not limited because it varies depending on the dosage forms, but when sulfated hyaluronic acid is made into injections, it is convenient for treatment of patients to adjust the concentration of the sulfated hyaluronic acid to 0.01 to 10% by weight/volume, preferably 0.05 to 1% by weight/volume in physiological saline. It is of course possible to prepare a concentrated preparation and make it into an injection as mentioned above immediately before use.

The optimal dose of sulfated hyaluronic acid as an effective ingredient varies depending on the age of patients, the kind and gravity of diseases, and dosage formes and administration routes, but in the case of intravenous injections, it can be 0.01 to 1,000 mg/kg, preferably 0.1 to 10 mg/kg. Nevertheless, since sulfated hyaluronic acid and other sulfated acid mucopolysaccharides and sulfated dextran do not show acute toxicity even at a dose of 2,000 mg/kg or more, they may be used beyond the above dose.

The preparation of the invention significantly reduces the number of mononuclear cells which infiltrated into the interstitial tissue of the kidney in a ureteral obstruction model animal made by the ligation of the ureter. Further, the preparation also suppresses the infiltration of leukocytes into the renal tissue in a model animal whose left renal artery was ligated.

Thus, the preparation has a prophylactic or therapeutic effect particularly on interstitial renal diseases such as reflux nephritides and diseases following the infiltration of leukocytes into the renal tissue, among renal diseases. Further, since the preparation exerts a medicinal effect by preventing the tissue infiltration of mononuclear cells, it is also useful for broad renal diseases such as glomerular renal diseases and lupus renal diseases wherein the expression of adhesive factors associated with the tissue infiltration of mononuclear cells is recognized. Further, since the tissue infiltration of mononuclear cells plays an important role also in the rejection of renal transplantation, the preparation exhibits efficacy by using it in place of or together with a usual immunosuppressant.

The invention is further detailedly described below by specific examples, but the invention should not be limited thereto.

Preparation Example 1 (sulfated hyaluronic acid)

High molecular hyaluronic acid (HMWHA; molecular weight 1,300 kDa) (200 mg) and 400 mg of sulfuric acid-trimethylamine complex (Aldrich) were dissolved in 6 ml of dimethylformamide, and the solution was stirred at 50 to 60° C. for one week in an oil bath. The reaction solution was concentrated under reduced pressure using a vacuum pump, the residue was dissolved in water, and the solution was dialyzed against deionized water overnight and freeze-dried. The resultant dry matter was dissolved in 2 ml of water, trifluoroacetic acid (an amount corresponding to 1.5 times the molar quantity of the total hydroxyl groups of HMWHA) was added, and the mixture was stirred at room temperature for one hour. After dialysis, the reaction solution was freeze-dried to give 200 mg of sulfated hyaluronic acid having a sulfation rate of about 60%.

Preparation Example 2 (sulfated dextran, etc.)

Although as sulfated dextran, one on the market (sodium dextran sulfate 5,000 etc., Wako Pure Chemical Industries, Ltd.) can be used, sulfated dextran having a desired molecular weight and a desired sulfation rate can be prepared according to the following way.

A sulfuric acid-trimethylamine composite (Aldrich) (2 g) was dissolved in 20 ml of dimethylformamide, 1 g of Dextran 40,000 (Wako Pure Chemical Industries, Ltd.) was suspended in the solution, and reaction was carried out at 60° C. for 3 days on a hot stirrer. The dextran which got to be a coagulum by the sulfation was dissolved in 5 ml of 1% sodium acetate, 5 volumes of acetone was added to form a precipitate (acetone precipitation method), and the precipitate was collected by centrifugation. The precipitate was vacuum dried, dissolved in 5 ml of distilled water, 3 g of trifluoroacetic acid was added, and the mixture was stirred at room temperature for 1 hour. The reaction solution was purified according to the above precipitation method to give about 900 mg of sulfated dextran as white powder. The sulfation rate was determined by the alkali titration of the sulfate radicals to be about 60%

By changing the molecular weight of dextran as a starting substance or the amount of the sulfating agent according to the above process, sulfated dextrans having various molecular weight values and various sulfation rates can be obtained. It is also possible to sulfate not only dextran but almost all polysaccharides such as chondroitin, chondroitin sulfate and dermatan sulfate according to the above process.

Assessment Test of Infiltration Into Renal Tissues (1) Wistar strain male rats weighing around 100 g (4 weeks old, each group consisting of 5 rats) were used. The rats were light anesthetized with diethyl ether, and the ureters were ligated to prepare renal disease model animals under the anesthetization according to Schreiner, et al. (Kidney Int. 34, 487–493, 1988).

A group wherein only a sham operation was carried out and the ureter was not ligated was assumed to be a control group. 2 mg each of the sulfated hyaluronic acid prepared according to the above Preparation example 1 (present invention) and non-sulfated hyaluronic acid (comparative example) were dissolved in 0.5 ml portions of physiological saline, respectively to give solutions as test samples.

An operation was carried out by subjecting each animal to ventrotomy, ablating the right ureter and ligating it with silk thread. Immediately after the operation, 2 mg/animal portions of each sample were intravenously injected into the animals from each tail vein. All the animals were killed 24 hours after the start of the experiment, and the number of cells which infiltrated into the interstitium of each animal was numerated by a micrometer. The results were expressed by the cell number per $mm^2$. The statistical analysis of the results was carried out according to Wilcoxon's test.

The results are shown in the following Table 1 (present invention) and Table 2 (comparison).

TABLE 1

Injection of Sulfated Hyaluronic Acid

| Animal | Weight | Hemocyte Number in Blood | Total Leukocyte Number | Monocyte Number | CD8 |
|---|---|---|---|---|---|
| a | 80 | 5525 | 162 | 128 | 26 |
| b | 80 | 5515 | 106 | 61 | 19 |
| c | 80 | 3350 | 118 | 58 | 16 |
| d | 100 | 3150 | 148 | 86 | 21 |
| e | 100 | 2400 | 96 | 68 | 18 |
| Average Value | 88 | 3988 | 126 | 80.2 | 20 |
| Standard Deviation | 9.797958971 | 1290.35886 | 25.07588 | 25.80233 | 3.405877 |
| SEM | 4.38178046 | 577.066027 | 11.21428 | 11.53915 | 1.523155 |

TABLE 2

Injection of Hyaluronic Acid

| Animal | Weight | Hemocyte Number in Blood | Total Leukocyte Number | Monocyte Number | CD8 |
|---|---|---|---|---|---|
| f | 80 | 5525 | 162 | 128 | 26 |
| g | 80 | 4400 | 236 | 182 | 45 |
| h | 80 | 3400 | 186 | 161 | 28 |
| i | 100 | 7500 | 181 | 148 | 41 |
| j | 100 | 7375 | 206 | 168 | 38 |
| Average Value | 88 | 5395 | 201 | 163.4 | 38.4 |
| Standard Deviation | 9.797958971 | 1704.14201 | 19.49359 | 11.30664 | 6.711.185 |
| SEM | 4.38178046 | 762.115477 | 8.717798 | 5.056481 | 3.001333 |

Note 1)

| | Hemocyte Number in Blood | Total Leukocyte Number | Monocyte Number | CD8 |
|---|---|---|---|---|
| Wilcoxon Test | 0.1508 | <0.0001 | <0.0001 | 0.0079 |
| T Test | 0.22448316 | 0.001497 | 0.000359 | 0.002418 |

It is seen from the above that sulfated hyaluronic acid significantly reduces the number of the cells which infiltrated in the animal model.

(2) An experiment was carried out using male SD rats (8 weeks old, one group consisting of 5 animals). Under anesthetization, each rat was subjected to ventrotomy, and the left renal artery was ligated. Sulfated hyaluronic acid (2 mg/body) was intravenously administered to the treatment group (n=5), and hyaluronic acid (2 mg/body) was intravenously administered to the control group (n=5). 45 minutes later, the renal artery was released and perfusion was started again, and 15 minutes later, each animal was slaughtered, the renal tissue was sampled, and freeze-dried sections were made. The number of leukocytes which infiltrated in the renal tissue was measured according to an enzyme-labeled antibody technique using a monoclonal antibody (OX1) against the rat leukocyte common antigen (CD45).

As a result, as shown below, leukocyte infiltration into the renal tissue was significantly suppressed in the sulfated hyaluronic acid administration group, compared with the hyaluronic acid administration group.

Average leukocyte number in the renal tissue in the sulfated hyaluronic acid administration group: 220/ $mm^2$ Average leukocyte number in the renal tissue in the hyaluronic acid administration group: 140/$mm^2$ From the foregoing, it is seen that sulfated hyaluronic acid suppresses leukocyte infiltration into the renal tissue after the renal ischemia reperfusion.

Further, other sulfated polysaccharides which can be prepared in the same manner as in the above Preparation example 2 can significantly reduce the number of cells which infiltrated, in the animal model.

Preparation Example

Pharmaceutical preparations each for intravenous, subcutaneous and intramuscular administration are prepared as follows, according to symptoms or conditions of patient:

(1) Sulfated hyaluronic acid was dissolved in a physiological saline solution for injection, so that the concentration of said sulfated hyaluronic acid might be 0.1–10% by weight based on the total weight of the resulting solution. The obtained solution was then subjected to a sterilization treatment in an autoclave at 121° C. for 20 minutes. Then, the solution was dispensed in a vial for injection which had previously been subjected to dry hot sterilization, and, thus, the captioned liquid preparations were each produced. The amount of the liquid preparation with which a vial is filled is usually 1, 2, 5, 10 and 20 ml.

(2) The above-mentioned liquid preparation may be freeze-dried and stored as a freeze-dried pharmaceutical preparation until immediately before use.

What is claimed is:

1. A method for the treatment of a renal disease which comprises administering a sulfated polysaccharide in an amount effective for the treatment of the renal disease to a mammal.

2. The method according to claim 1 wherein the renal disease is a disease in which mononuclear cells infiltrate into the renal tissue.

3. The method according to claim 1 wherein the renal disease is selected from the group consisting of an interstitial renal disease, a glomerular renal disease and a lupus renal disease.

4. The method according to claim 1 wherein the sulfated polysaccharide is a sulfated mucopolysaccharide or sulfated dextran.

5. The method according to claim 1 wherein the sulfated polysaccharide is sulfated hyaluronic acid.

6. The method according to claim 1 wherein the sulfated polysaccharide is sulfated hyaluronic acid wherein about 50 to 60% of the total hydroxyl groups of the hyaluronic acid is sulfated.

7. The method according to claim 1 wherein the sulfated polysaccharide is sulfated hyaluronic acid, and the renal disease is selected from the group consisting of an interstitial renal disease, a glomerular renal disease and a lupus renal disease.

8. The method according to claim 1 wherein the mammal is a human being.

* * * * *